(12) United States Patent
Samain et al.

(10) Patent No.: US 11,445,801 B2
(45) Date of Patent: Sep. 20, 2022

(54) TRANSFER DEVICE FOR MAKING UP KERATIN MATERIALS

(71) Applicant: L'OREAL, Paris (FR)

(72) Inventors: Henri Samain, Bievres (FR); Franck Giron, Lagny sur Marne (FR); Chrystele Gevrey, Sucy en Brie (FR)

(73) Assignee: L'OREAL, Paris (FR)

( * ) Notice: Subject to any disclaimer, the term of this patent is extended or adjusted under 35 U.S.C. 154(b) by 4 days.

(21) Appl. No.: 15/108,151

(22) PCT Filed: Jan. 19, 2014

(86) PCT No.: PCT/IB2014/067129
§ 371 (c)(1),
(2) Date: Jun. 24, 2016

(87) PCT Pub. No.: WO2015/097612
PCT Pub. Date: Jul. 2, 2015

(65) Prior Publication Data
US 2016/0324298 A1 Nov. 10, 2016

(30) Foreign Application Priority Data

Dec. 27, 2013 (FR) .................................... 1363642

(51) Int. Cl.
*A45D 40/30* (2006.01)
*A61K 8/02* (2006.01)
(Continued)

(52) U.S. Cl.
CPC ............ *A45D 40/30* (2013.01); *A61K 8/0204* (2013.01); *A61K 8/0208* (2013.01);
(Continued)

(58) Field of Classification Search
CPC .... A45D 40/30; A45D 40/00; A45D 2200/25; A45D 2200/1036; A45D 2029/005;
(Continued)

(56) References Cited

U.S. PATENT DOCUMENTS 2,746,460 A * 5/1956 Jellinek ................ A45D 29/001
132/73
4,137,180 A 1/1979 Naik et al.
(Continued)

FOREIGN PATENT DOCUMENTS

CN  1476319 A  2/2004
CN  1519278 A  8/2004
(Continued)

OTHER PUBLICATIONS

First Office Action for CN Pat. Appln. No. 201480076509.2 with English Translation dated Oct. 30, 2017, 9 pages.
(Continued)

*Primary Examiner* — Cris L. Rodriguez
*Assistant Examiner* — Brianne E Kalach
(74) *Attorney, Agent, or Firm* — Shumaker, Loop & Kendrick, LLP

(57) ABSTRACT

Process for making up an area of human keratin materials (P) using a makeup device having a transfer surface and a coat of at least one cosmetic colouring ink (4) borne by the transfer surface and obtained by printing using at least one digital printer, the colouring ink being intended to be applied to the keratin materials (P), the process comprising the following steps: —transferring at least part of the coat of cosmetic ink (4) onto the area (P) to be made up by placing the coat of ink (4) in contact with the area (P) to be made up, and then —forming a protective coating (8) by applying at least one composition comprising a film-forming polymer onto the area (P) of keratin materials to be made up.

14 Claims, 2 Drawing Sheets

(51) Int. Cl.
  *A61Q 1/02* (2006.01)
  *A61K 8/19* (2006.01)
  *B44C 1/17* (2006.01)
  *A45D 40/00* (2006.01)

(52) U.S. Cl.
  CPC .............. *A61K 8/0233* (2013.01); *A61K 8/19* (2013.01); *A61Q 1/02* (2013.01); *A61Q 1/025* (2013.01); *B44C 1/1733* (2013.01); *A45D 40/00* (2013.01); *A45D 2200/25* (2013.01)

(58) Field of Classification Search
  CPC .. A61K 8/0204; A61K 8/0208; A61K 8/0233; A61K 8/19; A61Q 1/02; A61Q 1/025; B44C 1/1733
  See application file for complete search history.

(56) References Cited

U.S. PATENT DOCUMENTS

| | | |
|---|---|---|
| 4,804,719 A | 2/1989 | Weaver et al. |
| 4,874,554 A | 10/1989 | Lange et al. |
| 4,903,840 A * | 2/1990 | So .................. A45D 29/001 206/581 |
| 4,925,567 A | 5/1990 | Faiiowa et al. |
| 4,925,667 A | 5/1990 | Fellows et al. |
| 4,936,325 A | 6/1990 | Davis |
| 4,999,418 A | 3/1991 | Krutak et al. |
| 5,030,708 A | 7/1991 | Krutak et al. |
| 5,032,670 A | 7/1991 | Parham et al. |
| 5,043,376 A | 8/1991 | Sharma et al. |
| 5,047,084 A | 9/1991 | Miller et al. |
| 5,078,160 A | 1/1992 | Carbonnier |
| 5,102,980 A | 4/1992 | Krutak et al. |
| 5,104,913 A | 4/1992 | Sharma et al. |
| 5,106,942 A | 4/1992 | Krutak et al. |
| 5,194,463 A | 3/1993 | Krutak et al. |
| 5,281,659 A | 1/1994 | Weaver et al. |
| 5,396,913 A | 3/1995 | Wallschlaeger |
| 5,421,765 A | 6/1995 | Lehmann et al. |
| 5,913,315 A | 6/1999 | Todd |
| 5,958,560 A | 9/1999 | Ewan |
| 5,997,134 A | 12/1999 | Hotomi et al. |
| 5,997,136 A | 12/1999 | Fujisawa et al. |
| 6,013,248 A | 1/2000 | Luebbe et al. |
| 6,106,852 A | 8/2000 | Vineberg |
| 6,168,656 B1 | 1/2001 | Schulz et al. |
| 6,190,730 B1 | 2/2001 | Matsos |
| 6,299,967 B1 | 10/2001 | Collins et al. |
| 6,312,124 B1 | 11/2001 | Desormeaux |
| 6,342,094 B1 | 1/2002 | Kabalnov |
| 6,367,484 B1 | 4/2002 | Ramin et al. |
| 6,428,164 B1 | 8/2002 | Missell et al. |
| 6,543,893 B2 | 4/2003 | Desormeaux |
| 6,622,733 B2 | 9/2003 | Saksa |
| 6,626,183 B1 * | 9/2003 | Pietrocola ............ A45D 29/001 132/73 |
| 7,241,503 B2 | 7/2007 | Noguchi |
| 7,648,364 B2 | 1/2010 | Dauga et al. |
| 3,007,062 A1 | 8/2011 | Edgar et al. |
| 8,083,422 B1 | 12/2011 | Simmons |
| 8,545,613 B2 | 10/2013 | Blette |
| 8,695,610 B2 | 4/2014 | Samain |
| 9,616,668 B1 | 4/2017 | Rabe |
| 2002/0020422 A1 | 2/2002 | Iosilevich |
| 2002/0035182 A1 | 3/2002 | L'Alloret et al. |
| 2002/0061321 A1* | 5/2002 | Bara ................ A61K 8/0241 424/401 |
| 2002/0110672 A1 | 8/2002 | Muratore-Pallatino et al. |
| 2002/0155069 A1 | 10/2002 | Pruche |
| 2002/0164295 A1 | 11/2002 | Scavone et al. |
| 2003/0053976 A1 | 3/2003 | Tournilhac et al. |
| 2004/0057742 A1 | 3/2004 | Richtsmeier |
| 2004/0078278 A1 | 4/2004 | Dauga |
| 2004/0241423 A1* | 12/2004 | Ramin ................ A61K 8/26 428/323 |
| 2004/0246327 A1* | 12/2004 | Elzi ........................ B41J 3/36 347/109 |
| 2005/0148908 A1 | 7/2005 | Stover |
| 2006/0093943 A1 | 5/2006 | Shu et al. |
| 2006/0098076 A1 | 5/2006 | Liang |
| 2006/0150994 A1* | 7/2006 | Pilmanis .............. A45D 40/30 132/218 |
| 2007/0144634 A1 | 6/2007 | Hitchcock |
| 2008/0031836 A1* | 2/2008 | Ilekti .................. A45D 29/001 424/61 |
| 2008/0053476 A1 | 3/2008 | LaHood et al. |
| 2008/0152681 A1 | 6/2008 | Brown et al. |
| 2008/0176160 A1 | 7/2008 | Deprez et al. |
| 2009/0325221 A1 | 12/2009 | Long et al. |
| 2010/0031834 A1 | 2/2010 | Morgavi et al. |
| 2010/0068247 A1 | 3/2010 | Mou et al. |
| 2010/0086693 A1 | 4/2010 | Yamada et al. |
| 2011/0020023 A1 | 1/2011 | Hirai |
| 2011/0025040 A1 | 2/2011 | Dominguez |
| 2011/0123703 A1 | 5/2011 | Mohammadi et al. |
| 2011/0141188 A1 | 6/2011 | Morita |
| 2011/0159463 A1 | 6/2011 | Samain |
| 2011/0164263 A1 | 7/2011 | Samain et al. |
| 2011/0268873 A1 | 11/2011 | Blette |
| 2012/0027423 A1 | 2/2012 | Kawai |
| 2012/0027443 A1 | 2/2012 | Kawai |
| 2012/0029417 A1 | 2/2012 | Samain et al. |
| 2012/0064011 A1 | 3/2012 | Schumann |
| 2012/0192884 A1 | 8/2012 | Nasu et al. |
| 2012/0244316 A1 | 9/2012 | Dobler et al. |
| 2012/0244465 A1 | 9/2012 | Kobayashi |
| 2012/0307304 A1 | 12/2012 | Moreno |
| 2013/0216295 A1 | 8/2013 | Ramin et al. |
| 2014/0233967 A1 | 8/2014 | Suzuki |
| 2015/0053759 A1 | 2/2015 | Cahill et al. |
| 2015/0150767 A1 | 6/2015 | Klug et al. |
| 2016/0000206 A1 | 1/2016 | Wong |
| 2016/0103962 A1 | 4/2016 | Costantino et al. |
| 2016/0316890 A1 | 11/2016 | Samain |
| 2016/0316891 A1 | 11/2016 | Samain |
| 2016/0316892 A1 | 11/2016 | Giron |
| 2016/0317403 A1 | 11/2016 | Giron |
| 2016/0324299 A1 | 11/2016 | Samain |
| 2019/0133300 A1 | 5/2019 | Hedglin |

FOREIGN PATENT DOCUMENTS

| | | |
|---|---|---|
| CN | 101010064 A | 8/2007 |
| CN | 101055605 A | 10/2007 |
| CN | 101686927 A | 3/2010 |
| CN | 101980694 A | 2/2011 |
| CN | 102490540 A | 6/2012 |
| DE | 102005050123 A1 | 4/2007 |
| EP | 705593 A1 | 4/1996 |
| EP | 0728460 A1 | 8/1996 |
| EP | 0749746 A1 | 12/1996 |
| EP | 0749747 A1 | 12/1996 |
| EP | 780114 A1 | 6/1997 |
| EP | 0923928 A1 | 6/1999 |
| EP | 0930060 A1 | 7/1999 |
| EP | 0938887 A1 | 9/1999 |
| EP | 1000607 A1 | 5/2000 |
| EP | 1048282 A1 | 11/2000 |
| EP | 1059047 A1 | 12/2000 |
| EP | 1304056 A2 | 4/2003 |
| EP | 1925278 A1 | 5/2008 |
| EP | 2090935 A1 | 8/2009 |
| FR | 2232303 A1 | 1/1975 |
| FR | 2759941 A1 | 8/1998 |
| FR | 2792192 A1 | 10/2000 |
| FR | 2858226 A1 | 2/2005 |
| FR | WO2006128737 | * 12/2006 |
| FR | 2900594 A | 8/2007 |
| FR | 2905630 A1 | 3/2008 |
| FR | 2909844 A1 | 6/2008 |
| FR | 2939033 A1 | 6/2010 |
| JP | S62180000 A | 8/1987 |
| JP | S63-188616 A | 8/1988 |
| JP | H-2503065 A | 9/1990 |

(56) References Cited

FOREIGN PATENT DOCUMENTS

| | | |
|---|---|---|
| JP | H04-208997 A | 7/1992 |
| JP | H11-007203 A | 1/1999 |
| JP | H11-169231 A | 6/1999 |
| JP | H-11169231 A | 6/1999 |
| JP | H11169231 A | 6/1999 |
| JP | H11-346828 A | 12/1999 |
| JP | 2001-245945 A | 9/2001 |
| JP | 2001278739 A | 10/2001 |
| JP | 3266197 B2 | 1/2002 |
| JP | 2002-058528 A | 2/2002 |
| JP | 2002068935 A | 3/2002 |
| JP | 2002-148998 A | 5/2002 |
| JP | 2003006452 A | 1/2003 |
| JP | 2004501177 A | 1/2004 |
| JP | 2004262913 A | 9/2004 |
| JP | 2005040356 A | 2/2005 |
| JP | 2005-088434 A | 4/2005 |
| JP | 2007204487 A | 8/2007 |
| JP | 2008-127388 A | 6/2008 |
| JP | 2010505843 A | 2/2010 |
| JP | 2010-186133 A | 8/2010 |
| JP | 2012-002869 A | 1/2012 |
| JP | 2012502908 A | 2/2012 |
| JP | 2012072081 A | 4/2012 |
| JP | 2012-518457 A | 8/2012 |
| JP | 2012518457 A | 8/2012 |
| JP | 2012-520837 A | 9/2012 |
| JP | 2012249849 A | 12/2012 |
| JP | 2013-031504 A | 2/2013 |
| JP | 2013137758 A | 7/2013 |
| JP | 2013532003 A | 8/2013 |
| JP | 2013-252709 A | 12/2013 |
| WO | 1992007913 A1 | 5/1992 |
| WO | 9848659 A1 | 5/1998 |
| WO | 02/36083 A1 | 5/2002 |
| WO | 03033270 A1 | 4/2003 |
| WO | 2006/128737 A1 | 12/2006 |
| WO | 2006128737 A1 | 12/2006 |
| WO | 2007/134171 A1 | 11/2007 |
| WO | 2010/004526 A1 | 1/2010 |
| WO | 2010004526 A1 | 1/2010 |
| WO | 2010004531 A1 | 1/2010 |
| WO | 2010/095118 A | 8/2010 |
| WO | 2010/105842 A2 | 9/2010 |
| WO | 2012081065 A1 | 6/2012 |
| WO | 2013093889 A2 | 6/2013 |
| WO | 2013126513 A1 | 8/2013 |
| WO | 2013178701 A2 | 12/2013 |

OTHER PUBLICATIONS

Final Rejection for U.S. Appl. No. 15/108,292 dated Jan. 30, 2018, 21 pages.
Non-Final Office Action in U.S. Appl. No. 15/108,192 dated Oct. 6, 2017 (6 pages).
Restriction Requirement for U.S. Appl. No. 15/108,303 dated Sep. 6, 2017 (7 pages).
Final Rejection for U.S. Appl. No. 15/108,076 dated Aug. 21, 2017.
Canon, fix your own printer, https://www.fixyourownprinter.com/posts/66407 (dated: Mar. 17, 2010) (1 page).
Non-Final Office Action for U.S. Appl. No. 15/108,292 dated Jul. 7, 2017.
Restriction and Election of Species Requirement in U.S. Appl. No. 15/108,292 dated Mar. 1, 2017 (8 pages).
Non-Final Office Action in U.S. Appl. No. 15/108,076 dated Mar. 16, 2017 (12 pages).
"Papilio Laser Printable Temporary Tattoo Paper" (http://www.papilio.com/laser temporary tattoo paper.html, Dec. 14, 2013 (3 pages).
"Cheap laser printer paper for toner transfer?" http://www.fountainpennetwork.com/forum/topic/41250-cheap-laser-printer-paper-for-toner-transfer/, Oct. 2, 2007 (11 pages).
International Search Report for PCT/IB2014/067130 dated Mar. 11, 2015 (5 pages).
International Search Report for PCT/IB2014/067132 dated Apr. 28, 2015 (4 pages).
International Search Report for PCT/IB2014/067133 dated Mar. 11, 2015 (5 pages).
International Search Report for PCT/IB2014/067134 dated Apr. 24, 2015 (4 pages).
International Search Report for PCT/IB2014/067136 dated Jul. 7, 2015 (5 pages).
International Search Report for PCT/IB2014/067138 dated Mar. 11, 2015 (3 pages).
International Search Report for PCT/IB2014/067129 dated Mar. 11, 2015 (6 pages).
Written Opinion for PCT/IB2014/067129 (4 pages).
Dyno Pretty Pup: "Dyno Pretty Pup Beauty Diary: LA Colors 30 Eye Design Palettes—Review." Mar. 16, 2012 (4 pages).
Office Action dated May 18, 2018 for Chinese Patent Application No. 2014800713416 (22 pages).
Office Action dated Apr. 23, 2018 in European Patent Application No. 14 833 256.2.
Apr. 12, 2018 Office Action issued in U.S. Appl. No. 15/108,303.
Non-Final Office Action for U.S. Appl. No. 15/108,302 dated Feb. 8, 2019 (7 pages).
Final Rejection for U.S. Appl. No. 15/108,295 dated Feb. 5, 2019 (10 pages).
Restriction Requirement for U.S. Appl. No. 15/108,305 dated Jan. 31, 2019 (8 pages).
English Translation of JP Office Action for JP Pat. App. No. 2016-542995 drafted Jan. 16, 2019 and dated Jan. 21, 2019 (3 pages).
Chinese Office Action dated Dec. 5, 2018 in Chinese Application No. 201480071307.9 (8 pages).
Japanese Office Action dated Nov. 19, 2018 for Japanese Application No. 2016-542996 (32 pages).
LA Colors 30 Eye Design Palettes- Review, Dyno Pretty Pup, http://dynopupbeauty.blogspot.n1/2012/03/la-colors-30-eye-design-palettes-review.html, Mar. 16, 2012 (5 pages).
Notice of Allowance dated Nov. 13, 2018 issued in U.S. Appl. No. 15/108,303 (27 pages).
Office Action for JP App. No. 2016-543027 dated Dec. 21, 2018 with English Translation (13 pages).
Office Action for JP App. No. 2016-543057 dated Dec. 17, 2018 with English Translation (14 pages).
Office Action issued in Chinese Application No. 201480071272.9 dated Jul. 2, 2018 (14 pp).
Office Action issued in U.S. Appl. No. 15/108,295 dated Aug. 6, 2018 (56 pp).
Office Action dated Jul. 2, 2018 issued in Japanese Patent Application No. 2016-543073 (17 pp).
Office Action dated Jun. 5, 2018 issued in Chinese Patent Application No. 201480074439.7 (16 pp).
Office Action dated Sep. 10, 2018 in Japanese Patent Application No. 2016-542897 (7 pages).
Office Action dated Sep. 27, 2018 in U.S. Appl. No. 15/108,292 (16 pages).
Pubchem; castor oil—https://pubchem.ncbi.nlm.nih.gov/compound/castor_oil#section=Top; 1 page; 2010.
Non-Final Office Action for U.S. Appl. No. 15/108,294 dated Mar. 4, 2019 (11 pgs.).
Office Action for JP App. No. 2016-543072 dated Dec. 17, 2018 with English Translation(7 pages).
Office Action for JP App. No. 2016-543056 dated Dec. 17, 2018 with English Translation (7 pages).
Japanese Office Action for JP Pat. Appln. No. 2016-543057 dated Aug. 26, 2019 (8 pages).
Notice of Allowance for U.S. Appl. No. 15/108,292 dated Aug. 29, 2019 (16 pages).
Japanese Office Action for JP Pat. Appln. No. 2016-543056 dated Aug. 26, 2019 (8 pages).
Japanese Office Action for JP Pat. Appln. No. 2016-542996 dated Sep. 2, 2019 (14 pages).

(56) References Cited

OTHER PUBLICATIONS

Final Rejection for U.S. Appl. No. 15/108,292 dated Apr. 26, 2019 (7 pages).
Non-Final Office Action for U.S. Appl. No. 15/108,295 dated Jan. 31, 2020 (14 pages).
Examiner's Answer in response to Appeal Brief filed Dec. 4, 2019 for U.S. Appl. No. 15/108,302, dated Feb. 4, 2020 (7 pages).
Non-Final Office Action for U.S. Appl. No. 15/108,305 dated May 15, 2019 (17 pages).
Japanese Office Action for JP Patent App. No. 2016-543072 dated Mar. 12, 2020 with English translation (7 pages).
Non-Final Office Action for U.S. Appl. No. 15/108,295 dated Jun. 6, 2019 (12 pages).
Final Rejection for U.S. Appl. No. 15/108,302 dated Jul. 2, 2019 (7 pages).
Notice of Allowance for U.S. Appl. No. 15/108,294 dated Jul. 25, 2019 (9 pages).
Japanese Office Action for JP Pat. Appln. No. 2016-542897, dated Sep. 17, 2019 (10 pages).
Final Rejection for U.S. Appl. No. 15/108,305, dated Mar. 3, 2020 (24 pages).
Non-Final Office Action for U.S. Appl. No. 15/108,295 dated (15 pages).
Non-Final Office Action for U.S. Appl. No. 15/108,305, dated Jan. 6, 2021 (14 pgs.).
Patent Board Decision—Examiner Affirmed for U.S. Appl. No. 15/108,302, dated Jan. 8, 2021 (10 pgs.).
Restriction Requirement for U.S. Appl. No. 16/694,035, dated Jan. 12, 2021 (8 pgs.).
Japanese Office Action for 2019-127617 dated Jun. 22, 2020 with English Translation (9 pages).
Final Rejection for U.S. Appl. No. 15/108,295 dated Jun. 15, 2020 (12 pages total).
Final Rejection for U.S. Appl. No. 15/108,305 dated Jun. 15, 2021 (15 pages).
Final Rejection for U.S. Appl. No. 15/108,295 dated Apr. 2, 2021 (18 pages).
Office Action for Korean Patent App. No. 10-2016-7020078 dated Jan. 27, 2021 with English Translation (14 pages).
Non-Final Office Action for U.S. Appl. No. 15/108,302 dated Apr. 22, 2021 (10 pages).
Non-Final Office Action for U.S. Appl. No. 16/694,035 dated May 10, 2021 (7 pages).
Korean Office Action for KR Pat. Appln. No. 10-2016-7020687, dated Feb. 25, 2021 with English Translation (22 pages).
European Office Action for EP Pat. Appln. No. 14833254.7 dated Aug. 30, 2021 (5 pages).
Corrected Notice of Allowance for U.S. Appl. No. 15/108,302 dated Sep. 8, 2021 (2 pages).
Notice of Allowance for U.S. Appl. No. 15/108,302 dated Aug. 23, 2021 (9 pages).
Supplemental Notice of Allowance for U.S. Appl. No. 15/108,295 dated Aug. 11, 2021 (6 pages).
Notice of Allowance for U.S. Appl. No. 15/108,295, dated Aug. 5, 2021 (10 pages).
Japanese Office Action for JP Pat. Appln. No. 2019-127617, drafted Aug. 12, 2021 and dated Sep. 6, 2021 with English Translation (11 pages).
Notice of Allowance for U.S. Appl. No. 15/108,305, dated Sep. 30, 2021 (13 pages).
Corrected Notice of Allowability for U.S. Appl. No. 15/108,302, dated Sep. 29, 2021 (2 pages).
Corrected Notice of Allowability for U.S. Appl. No. 15/108,302, dated Sep. 14, 2021 (2 pages).
Final Rejection issued for U.S. Appl. No. 16/694,035, dated Oct. 1, 2021 (11 pages).
Non-Final Office Action for U.S. Appl. No. 16/694,035, dated Jul. 6, 2022 (8 pages).

* cited by examiner

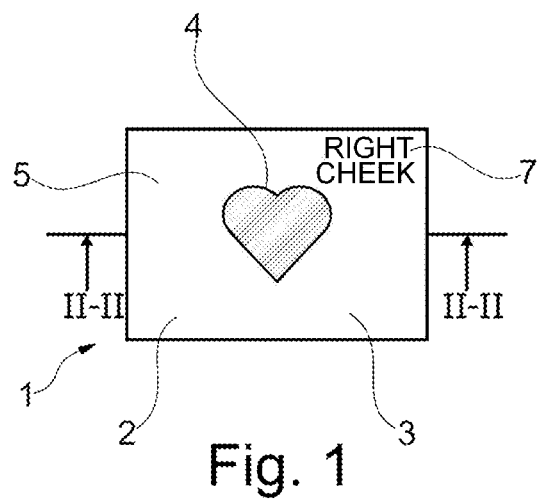
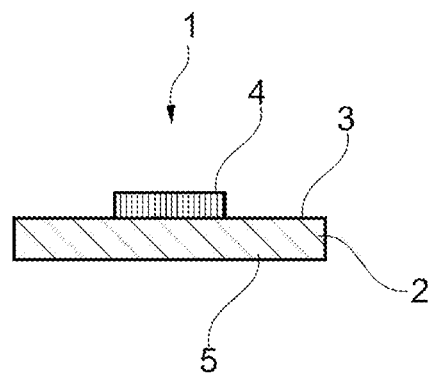
Fig. 1
Fig. 2
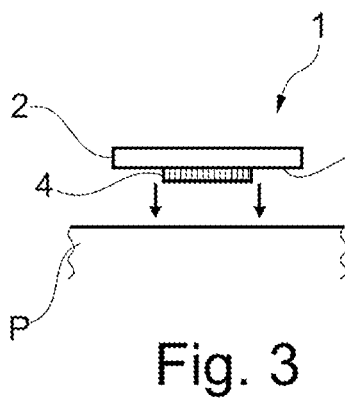 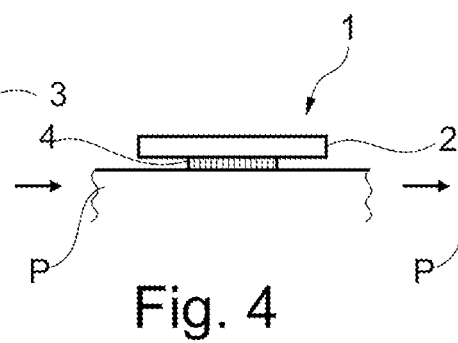 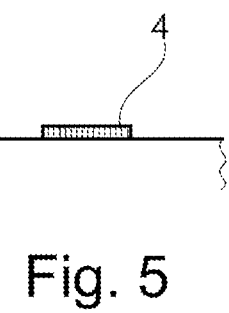
Fig. 3    Fig. 4    Fig. 5
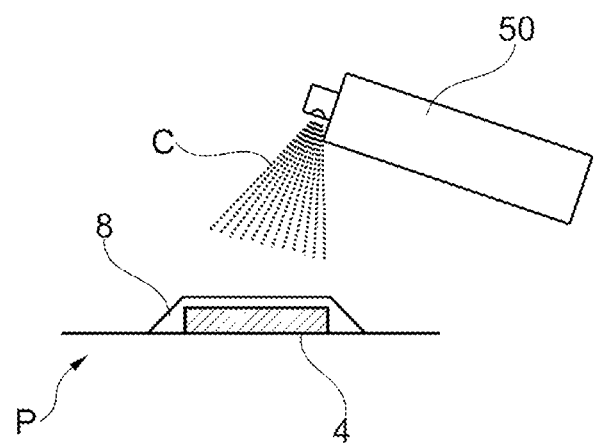
Fig. 6

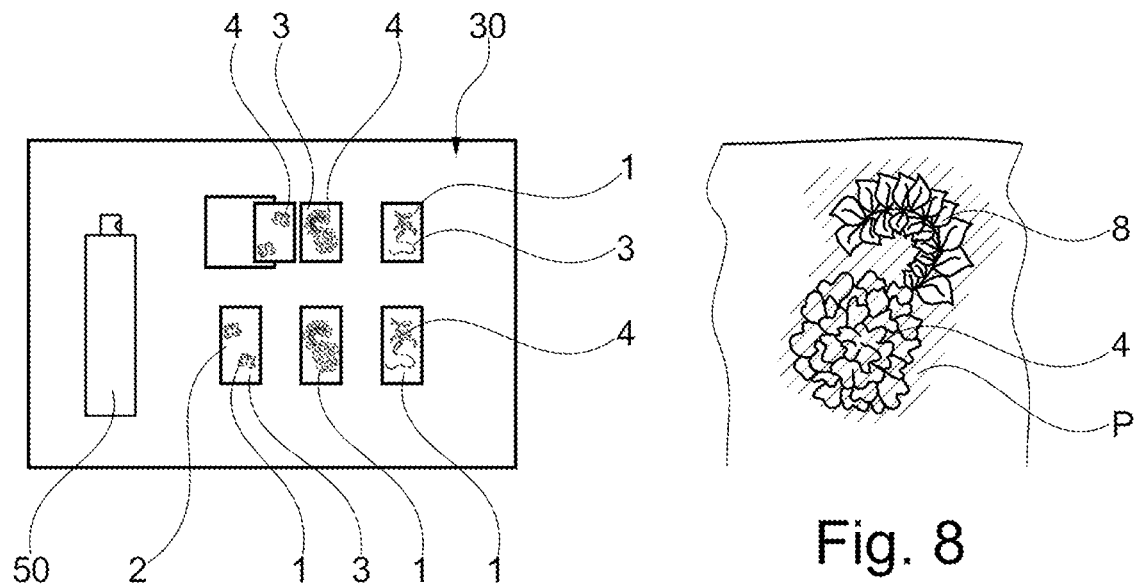
Fig. 7
Fig. 8
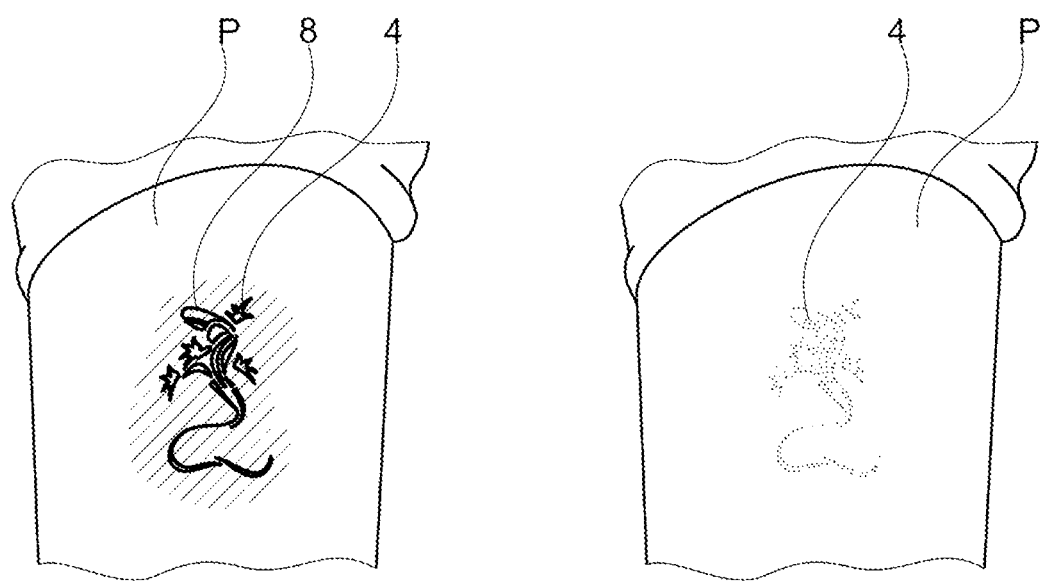
Fig. 9a          Fig. 9b

TRANSFER DEVICE FOR MAKING UP KERATIN MATERIALS

The present invention relates to makeup application by transfer.

BACKGROUND

There is a need to cover keratin materials, especially the skin or the lips, with precisely deposited coatings, such as patterns, at the millimetre scale.

However, no practical and efficient method exists. Drawing a pattern takes a long time to do and requires the intervention of a professional makeup artist. Methods using a patch or a decal transfer are disappointing, since the number of patterns is limited and it is difficult to avoid folds in the support bearing the pattern. This technique is, in particular, unsuitable for the face. On account of the movements of the facial skin, the support becomes cracked, thus giving a degraded and unaesthetic visual result.

Furthermore, once these patterns have been produced, it is desired to preserve their precision and the quality of the contrast with respect to the various possible attacking factors such as sweat or rain, or the simple fact of touching the skin or other possible contacts (clothing, hair, etc.).

There is a need to protect the patterns produced on keratin materials in order to benefit from the quality of the pattern in the hours that follow, or even for several days.

There is also a need to have available makeup patterns intended to cover a small area or indeed the entire area of the face or the lips.

There is also a need to propose to each user a wide variety of patterns, colours, shapes and distributions, or even to propose to the user to define his patterns, so as best to satisfy his particular request, without the need to have a large number of references at hand.

In addition, it is also desirable for the pattern, once transferred onto keratin materials, especially the skin, to remain relatively stable. In other words, either immediately after transferring or, for example, within an hour of transferring, it is advantageous for the made-up area to be able to be touched, especially with the fingers, without deteriorating the pattern produced.

However, conventionally produced makeup coatings may not have satisfactory stability in this regard.

This lack of stability is not necessarily a problem, since high precision of the makeup pattern is not sought. On the other hand, in the case of precisely deposited patterns, it is important for the makeup obtained after transferring to be stable.

There is thus a need to prepare the area to be made up so that the transfer keeps its precision intact.

The present invention is directed toward meeting all or some of these needs.

SUMMARY

According to a first aspect, the present invention relates to a process for making up an area of human keratin materials using a makeup device having a transfer surface and a coat of at least one cosmetic colouring ink borne by the transfer surface and obtained by printing using at least one digital printer, the colouring ink being intended to be applied to the keratin materials, the process comprising the following steps:

transferring at least part of the coat of cosmetic ink onto the area to be made up by placing the coat of ink in contact with the area to be made up, and then forming a protective coating by applying at least one cosmetic composition comprising a film-forming polymer onto the area of keratin materials to be made up.

The process may also comprise a step that consists in moving the transfer surface away from the area of the human keratin materials after the coat of ink has been transferred.

The makeup area may be an area of skin, especially of the face, the scalp, the nails or the lips.

By means of the invention, the user can decorate and/or treat the skin, the lips, the nails or the hair uniformly or with patterns.

The use of a coat of cosmetic ink obtained by printing using a printer advantageously makes it possible, when compared with standard makeup applications, to obtain a complex and customizable application.

The use of a protective coating is especially useful for benefiting from the quality of the pattern within the hours that follow, or even for several days, in particular for making up the body or the nails.

The process according to the invention makes it possible to cover small areas such as the lips or the nails.

The process according to the invention is compatible with the usual treatments for covering keratin materials.

The ink borne by the transfer surface preferably comprises a dyestuff.

The transfer surface is, for example, an outer surface of a substrate.

Protective Coating

The protective coating may be colourless or coloured.

The protective coating may be translucent or transparent, preferably transparent.

Preferentially, the protective coating is at least partly produced using a fluid composition. The fluid composition has, for example, a viscosity ranging from 1 mPa·s to 500 mPa·s and preferably from 1 mPa·s to 300 mPa·s at 25° C.

The viscosity may be measured via any process known to those skilled in the art, and especially according to the following conventional process. At 25° C. using a Rheomat 180 viscometer, equipped with a spindle rotating at 200 rpm, a person skilled in the art can select the spindle for measuring the viscosity from the spindles M1, M2, M3 and M4 on the basis of their general knowledge, so as to be able to perform the measurement.

Solvents

The fluid composition of the protective coating especially comprises a solvent chosen so as not to be able to dissolve or disperse the dyestuffs of the ink.

The fluid composition may comprise at least one aqueous or organic solvent, especially a volatile organic solvent.

The fluid composition may advantageously comprise a volatile solvent, especially water or a volatile organic solvent.

For the purposes of the present invention, the term "volatile solvent" means a solvent that is liquid at room temperature, especially having a non-zero vapour pressure, at room temperature and atmospheric pressure, in particular having a vapour pressure ranging from 0.13 Pa to 40 000 Pa (10-3 to 300 mmHg), preferably ranging from 1.3 Pa to 13 000 Pa (0.01 to 100 mmHg), and preferentially ranging from 1.3 Pa to 1300 Pa (0.01 to 10 mmHg).

The content of water-insoluble volatile compound that is liquid at room temperature is, for example, from 5% to 95%, especially from 10% to 80% and in particular from 30% to 70% by weight relative to the total weight of the composition.

For the purposes of the invention, the expression "volatile compound" means any compound (or non-aqueous medium) that is capable of evaporating on contact with the skin or keratin fibres in less than one hour, at room temperature and atmospheric pressure.

In contrast, the term "non-volatile compound" refers to a compound that remains on keratin materials, at room temperature and atmospheric pressure, for at least several hours and which especially has a vapour pressure of less than $10^{-3}$ mmHg (0.13 Pa).

The volatile organic solvent of the fluid composition may in particular comprise a cosmetically acceptable oil, or a mixture of such compounds. The term "cosmetically acceptable" means a compound whose use is compatible with application to keratin materials.

When the fluid composition comprises one or more organic solvents, these solvents may be present in a content ranging from 20% to 99% and preferably from 40% to 95% relative to the total weight of the composition.

The fluid composition may comprise at least one volatile solvent consisting of a volatile oil.

The oil may be a silicone oil or a hydrocarbon-based oil, or may comprise a mixture of such oils.

For the purposes of the present invention, the term "silicone oil" means an oil comprising at least one silicon atom, and especially at least one Si—O group.

The term "hydrocarbon-based oil" means an oil mainly containing hydrogen and carbon atoms and possibly oxygen, nitrogen, sulfur and/or phosphorus atoms.

The volatile hydrocarbon-based oils may be chosen from hydrocarbon-based oils containing from 8 to 16 carbon atoms, and especially branched $C_8$-$C_{16}$ alkanes (also known as isoparaffins), for instance isododecane (also known as 2,2,4,4,6-pentamethylheptane), isodecane, isohexadecane and, for example, the oils sold under the trade names Isopar® or Permethyl®.

Volatile oils that may also be used include volatile silicones, for instance volatile linear or cyclic silicone oils, especially those with a viscosity centistokes ($8 \times 10^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of linear volatile alkyltrisiloxane oils of general formula (I):

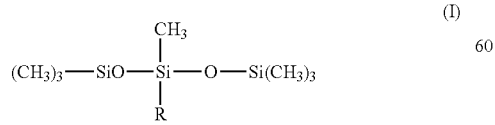

(I)

in which R represents an alkyl group comprising from 2 to 4 carbon atoms, one or more hydrogen atoms of which may be replaced with a fluorine or chlorine atom.

Among the oils of general formula (I), mention may be made of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

A composition according to the invention may comprise, for example, between 1% and 95% by weight and better still between 5% and 75% by weight of volatile oil relative to the total weight of the composition.

The fluid composition may comprise at least one organic solvent chosen from the following list:
ketones that are liquid at room temperature, such as methyl ethyl ketone, methyl isobutyl ketone, diisobutyl ketone, isophorone, cyclohexanone or acetone;
alcohols that are liquid at room temperature, such as ethanol, isopropanol, diacetone alcohol, 2-butoxy-ethanol or cyclohexanol;
glycols that are liquid at room temperature, such as ethylene glycol, propylene glycol, pentylene glycol or glycerol;
propylene glycol ethers that are liquid at room temperature, such as propylene glycol monomethyl ether, propylene glycol monomethyl ether acetate or dipropylene glycol n-butyl ether;
short-chain esters, containing from 3 to 8 carbon atoms in total, such as ethyl acetate, methyl acetate, propyl acetate, n-butyl acetate or isopentyl acetate;
alkanes that are liquid at room temperature, such as decane, heptane, dodecane and cyclohexane.

The non-aqueous solvent medium may also comprise at least one non-volatile, water-insoluble compound that is liquid at room temperature, especially at least one non-volatile oil, which may be chosen in particular from non-volatile hydrocarbon-based oils and/or silicone oils.

Non-volatile hydrocarbon-based oils that may especially be mentioned include:
hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil and musk rose oil; or else caprylic/capric acid triglycerides, for instance those sold by the company Stéarineries Dubois or those sold under the names Miglyol 810, 812 and 818 by the company Dynamit Nobel;
synthetic ethers containing from 10 to 40 carbon atoms;
linear or branched hydrocarbons of mineral or synthetic origin, such as petroleum jelly, polydecenes, hydrogenated polyisobutene such as Parleam, and squalane, and mixtures thereof;
synthetic esters such as oils of formula $R_1COOR_2$ in which $R_1$ represents a linear or branched fatty acid residue containing from 1 to 40 carbon atoms and $R_2$ represents an in particular branched hydrocarbon-based chain containing from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;

fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol;

higher fatty acids such as oleic acid, linoleic acid or linolenic acid;

and mixtures thereof.

The non-volatile silicone oils that can be used in the composition according to the invention may be non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

According to one embodiment, the composition according to the invention may comprise water and/or at least one water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the compositions according to the invention are generally also volatile.

Among the water-soluble solvents that may be used in the compositions according to the invention, mention may be made especially of lower monoalcohols containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

The water and/or the water-soluble solvent(s) may be introduced as such into the composition according to the invention or may be incorporated therein by means of one or more ingredients constituting the said composition. Thus, water may especially be introduced into the composition by means of introducing an aqueous dispersion of polymer particles that is useful, for example, as a film-forming agent.

The content of water and/or of water-soluble solvent(s) in the fluid composition of the invention may in particular range from 0.1% to 80% and more particularly from 2% to 70% by weight relative to the total weight of the fluid composition.

The composition of the protective coating according to the invention may comprise a solvent and a material which, after disappearance of the solvent, for example by evaporation or absorption, produces a protective film that isolates the transferred pattern from the external environment.

The protective film may or may not be continuous.

The protective film may have a greasy or dry feel.

Film-Forming Polymers

Advantageously, the composition of the protective coating according to the invention comprises a film-forming polymer.

The film-forming polymer may be a polymer that is dissolved or dispersed in the form of particles in an aqueous phase of the composition or alternatively dissolved or dispersed in the form of particles in a liquid fatty phase. The composition may comprise a mixture of these polymers.

The film-forming polymer may be present in the composition according to the invention in a solids content ranging from 0.01% to 20% by weight and preferably from 0.5% to 10% by weight relative to the total weight of the composition.

In the present application, the term "film-forming polymer" means a polymer that is capable of forming, by itself or in the presence of an auxiliary film-forming agent, a continuous and adherent film on a support, especially on keratin materials.

Use is preferably made of a film-forming polymer capable of forming a hydrophobic film, i.e. a polymer for which the film has a solubility in water at 25° C. of less than 1% by weight.

Among the film-forming polymers that may be used in the composition of the present invention, mention may be made of synthetic polymers, of free-radical type or of polycondensate type, polymers of natural origin, and mixtures thereof.

The expression "free-radical film-forming polymer" means a polymer obtained by polymerization of unsaturated and especially ethylenically unsaturated monomers, each monomer being capable of homopolymerizing (unlike polycondensates).

The film-forming polymers of free-radical type may be, in particular, vinyl polymers or copolymers, in particular acrylic polymers.

The vinyl film-forming polymers may result from the polymerization of ethylenically unsaturated monomers containing at least one acid group and/or esters of these acid monomers and/or amides of these acid monomers.

As monomer bearing an acid group, use may be made of α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acid monomers are advantageously chosen from (meth)acrylic acid esters (also known as (meth)acrylates), in particular alkyl (meth)acrylates, in particular $C_1$-$C_{30}$ and preferably $C_1$-$C_{20}$ alkyl (meth)acrylates, aryl (meth)acrylates, in particular $C_6$-$C_{10}$ aryl (meth)acrylates, and hydroxyalkyl (meth)acrylates, in particular $C_2$-$C_6$ hydroxyalkyl (meth)acrylates.

Mention may be made, among alkyl (meth)acrylates, of methyl methacrylate, ethyl methacrylate, butyl methacrylate, isobutyl methacrylate, 2-ethylhexyl methacrylate, lauryl methacrylate or cyclohexyl methacrylate.

Mention may be made, among hydroxyalkyl (meth)acrylates, of hydroxyethyl acrylate, 2-hydroxypropyl acrylate, hydroxyethyl methacrylate or 2-hydroxypropyl methacrylate.

Mention may be made, among aryl (meth)acrylates, of benzyl acrylate and phenyl acrylate.

The (meth)acrylic acid esters which are particularly preferred are the alkyl (meth)acrylates.

According to the present invention, the alkyl group of the esters can be either fluorinated or perfluorinated, that is to say that a portion or all of the hydrogen atoms of the alkyl group are replaced by fluorine atoms.

Mention may be made, as amides of the acid monomers, for example, of (meth)acrylamides and in particular N-alkyl (meth)acrylamides, especially N—($C_2$-$C_{12}$ alkyl)(meth)

acrylamides. Mention may be made, among the N-alkyl (meth)acrylamides, of N-ethylacrylamide, N-(t-butyl) acrylamide, N-(t-octyl)acrylamide and N-undecylacrylamide.

The vinyl film-forming polymers may also result from the homopolymerization or copolymerization of monomers chosen from vinyl esters and styrene monomers. In particular, these monomers may be polymerized with acid monomers and/or esters thereof and/or amides thereof, such as those mentioned previously.

Examples of vinyl esters that may be mentioned are vinyl acetate, vinyl neodecanoate, vinyl pivalate, vinyl benzoate and vinyl t-butylbenzoate.

Styrene monomers that may be mentioned include styrene and α-methyl styrene.

It is possible to use any monomer known to those skilled in the art included in the categories of acrylic and vinyl monomers (including monomers modified with a silicone chain).

Among the film-forming polycondensates that may be mentioned are polyurethanes, polyesters, polyesteramides, polyamides, epoxyester resins and polyureas.

The polyurethanes may be chosen from anionic, cationic, nonionic and amphoteric polyurethanes, polyurethane-acrylics, polyurethane-polyvinyl-pyrrolidones, poly-ester-polyurethanes, polyether-polyurethanes, polyureas and polyurea-polyurethanes, and mixtures thereof.

The polyesters may be obtained, in a known manner, by polycondensation of dicarboxylic acids with polyols, in particular diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid, 2,6-naphthalenedicarboxylic acid. These dicarboxylic acid monomers may be used alone or as a combination of at least two dicarboxylic acid monomers. Among these monomers, the ones preferentially chosen are phthalic acid, isophthalic acid and terephthalic acid.

The diol may be chosen from aliphatic, alicyclic and aromatic diols. The diol used is preferably chosen from: ethylene glycol, diethylene glycol, triethylene glycol, 1,3-propanediol, cyclohexanedimethanol and 4-butanediol.

Other polyols that may be used are glycerol, pentaerythritol, sorbitol and trimethylolpropane.

The polyesteramides may be obtained in a manner analogous to that of the polyesters, by polycondensation of diacids with diamines or amino alcohols. Diamines that may be used are ethylenediamine, hexamethylenediamine and meta- or para-phenylenediamine. An amino alcohol that may be used is monoethanolamine.

The polyester may also comprise at least one monomer bearing at least one group —$SO_3M$, with M representing a hydrogen atom, an ammonium ion $NH_4^+$ or a metal ion, for instance an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ may be used in particular.

The aromatic nucleus of the difunctional aromatic monomer also bearing a group —$SO_3M$ as described above may be chosen, for example, from benzene, naphthalene, anthracene, biphenyl, oxybiphenyl, sulfonylbiphenyl and methylenebiphenyl nuclei.

As examples of difunctional aromatic monomers also bearing a group —$SO_3M$, mention may be made of: sulfoisophthalic acid, sulfoterephthalic acid, sulfophthalic acid and 4-sulfonaphthalene-2,7-dicarboxylic acid.

The copolymers preferably used are those based on isophthalate/sulfoisophthalate, and more particularly copolymers obtained by condensation of diethylene glycol, cyclohexanedimethanol, isophthalic acid and sulfoisophthalic acid. Such polymers are sold for example under the trade name Eastman AQ® by the company Eastman Chemical Products.

The polymers of natural origin, optionally modified, may be chosen from shellac resin, sandarac gum, dammar resins, elemi gums, copal resins and cellulose-based polymers, and mixtures thereof.

According to a first embodiment of the composition according to the invention, the film-forming polymer may be present in the form of particles in aqueous dispersion, which is generally known as a latex or pseudolatex. Techniques for preparing these dispersions are well known to those skilled in the art.

Aqueous dispersions of film-forming polymer that may be used include the acrylic dispersions sold under the names Neocryl XK-90®, Neocryl A-1070®, Neocryl A-1090®, Neocryl BT-62®, Neocryl A-1079®, Neocryl A-523® by the company Avecia-Neoresins, Dow Latex 432® by the company Dow Chemical, Daitosol 5000 AD® by the company Daito Kasey Kogyo; or else the aqueous polyurethane dispersions sold under the names Neorez R-981®, Neorez R-974® by the company Avecia-Neoresins, Avalure UR-405®, Avalure UR-410®, Avalure UR-425®, Avalure UR-450®, Sancure 875®, Sancure 861 ®, Sancure 878 ®, Sancure 2060® by the company Goodrich, Impranil 85® by the company Bayer, Aquamere H-1511 ® by the company Hydromer.

Use may also be made, as aqueous dispersions of film-forming polymer, of the dispersions of polymers resulting from the free-radical polymerization of one or more free-radical monomers inside and/or partially at the surface of pre-existing particles of at least one polymer chosen from the group consisting of polyurethanes, polyureas, polyesters, polyesteramides and/or alkyds. These polymers are generally referred to as "hybrid polymers".

According to a second embodiment variant of the composition according to the invention, the film-forming polymer may be a water-soluble polymer and is therefore present in the aqueous phase of the composition in dissolved form. Examples of water-soluble film-forming polymers that may be mentioned include:

proteins, for instance proteins of plant origin such as wheat proteins and soybean proteins; proteins of animal origin such as keratins, for example keratin hydrolysates and sulfonic keratins;

anionic, cationic, amphoteric or nonionic chitin or chitosan polymers;

cellulose polymers such as hydroxyethyl cellulose, hydroxypropyl cellulose, methyl cellulose, ethyl hydroxyethyl cellulose and carboxymethyl cellulose, and also quaternized cellulose derivatives;

acrylic polymers or copolymers, such as polyacrylates or polymethacrylates;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

optionally modified polymers of natural origin, such as: gum arabic, guar gum, xanthan derivatives, karaya gum; alginates and carrageenans;

glycosaminoglycans, hyaluronic acid and derivatives thereof;

shellac resin, sandarac gum, dammar resins, elemi gums and copal resins;

deoxyribonucleic acid;

mucopolysaccharides such as hyaluronic acid and chondroitin sulfates, and mixtures thereof.

According to another embodiment variant of the composition of the protective coating according to the invention, the film-forming polymer may be present in a liquid fatty phase comprising organic solvents or oils such as those described above. For the purposes of the invention, the term "liquid fatty phase" means a fatty phase that is liquid at room temperature (25° C.) and atmospheric pressure (760 mmHg, i.e. $10^5$ Pa), composed of one or more fatty substances that are liquid at room temperature, also known as oils, which are generally mutually compatible.

Preferably, the liquid fatty phase comprises a volatile oil, optionally mixed with a non-volatile oil, the oils possibly being chosen from the oils mentioned above.

According to a third embodiment of the composition according to the invention, the film-forming polymer may be present in the form of surface-stabilized particles that are dispersed in the liquid fatty phase.

The dispersion of surface-stabilized polymer particles may be manufactured as described in document EP-A-749 747.

The polymer particles are surface-stabilized by means of a stabilizer that may be a block polymer, a grafted polymer and/or a random polymer, alone or as a mixture.

Dispersions of film-forming polymer in the liquid fatty phase, in the presence of stabilizers, are especially described in documents EP-A-749 746, EP-A-923 928 and EP-A-930 060, the content of which is incorporated by reference into the present patent application.

The size of the polymer particles in dispersion, either in the aqueous phase or in the liquid fatty phase, may range from 5 nm to 600 nm, and preferably from 20 nm to 300 nm.

According to a fourth embodiment of the composition of the protective coating according to the invention, the film-forming polymer may be dissolved in the liquid fatty phase, in which case the film-forming polymer is said to be a liposoluble polymer.

Examples of liposoluble polymers that may be mentioned are copolymers of a vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (in which the alkyl group comprises from 2 to 18 carbon atoms) or an allyl or methallyl ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Examples of these copolymers that may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene crosslinked with 0.2% divinylbenzene, and allyl propionate/allyl stearate, crosslinked with 0.2% divinylbenzene.

Liposoluble film-forming polymers that may also be mentioned include liposoluble homopolymers, and in particular those resulting from the homopolymerization of vinyl esters containing from 9 to 22 carbon atoms or of alkyl acrylates or methacrylates, the alkyl radicals containing from 10 to 20 carbon atoms.

Such liposoluble homopolymers may be chosen from polyvinyl stearate, polyvinyl stearate crosslinked with the aid of divinylbenzene, of diallyl ether or of diallyl phthalate, polystearyl (meth)acrylate, polyvinyl laurate and polylauryl (meth)acrylate, it being possible for these poly(meth)acrylates to be crosslinked with the aid of ethylene glycol dimethacrylate or tetraethylene glycol dimethacrylate.

The liposoluble copolymers and homopolymers defined previously are known and are described in particular in patent application FR-A-2 232 303; they may have a weight-average molecular weight ranging from 2000 to 500 000 and preferably from 4000 to 200 000.

As liposoluble film-forming polymers that may be used in the invention, mention may also be made of polyalkylenes and in particular copolymers of $C_2$-$C_{20}$ alkenes, such as polybutene, alkyl celluloses with a linear or branched, saturated or unsaturated $C_1$-$C_8$ alkyl radical, for instance ethyl cellulose and propyl cellulose, copolymers of vinylpyrrolidone (VP) and in particular copolymers of vinylpyrrolidone and of $C_2$ to $C_{40}$ and better still $C_3$ to $C_{20}$ alkene. As examples of VP copolymers that may be used in the invention, mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

The composition of the protective coating according to the invention may comprise an auxiliary film-forming agent that promotes the formation of a film with the film-forming polymer. Such a film-forming agent may be chosen from any compound known to those skilled in the art as being capable of fulfilling the desired function, and may be chosen especially from plasticizers and coalescers.

System for Applying the Protective Coating

To form the protective coating, the composition may be applied using any system for applying a cosmetic product to keratin materials that is known to those skilled in the art.

The application system is advantageously chosen to allow careful application of the composition.

A manual application system that may be used in the context of the invention is, for example, a fine or coarse brush, a pad of cotton wool or a wipe.

Preferably, the application system is a propulsion system that advantageously allows faster application of the composition and that does not deteriorate the precision of the pattern formed by the transferred coat of ink.

The propulsion application system may be configured to deliver a composition in liquid (spray) form, being chosen, for example, from a pressurized system, a pump-dispenser bottle, a Venturi system, an electrostatic-attraction system and a vibrating system. Advantageously, such an application system affords rapid drying of the composition.

In one variant, the propulsion application system is configured to spray the composition in pulverulent form. This embodiment is particularly advantageous for making up certain areas of the body for which the use of a spray is undesirable and/or difficult.

The protective coating may be prepared by applying one or more coats, each of identical or different composition.

Cosmetic Ink—Dyestuff

The dyestuff may comprise one or more dyes as described below.

The dyestuff may be present in the ink in a mass content ranging from 0.01% to 60%, preferably ranging from 0.1% to 40%, or even from 0.1% to 30% and preferentially ranging from 0.5% to 20%, relative to the total mass of the ink.

The colouring ink may comprise one or more dyestuffs chosen from water-soluble dyes, liposoluble dyes, pulverulent dyestuffs such as pigments, especially nacres, and glitter flakes, or alternatively colouring polymers.

The term "pigments" should be understood as meaning white or coloured, mineral or organic particles of any form, which are insoluble in the cosmetic medium, and which are intended to colour the cosmetic ink.

The term "nacres" should be understood as meaning iridescent particles of any shape, in particular produced by certain molluscs in their shell, or else synthesized.

The pigments may be white, black or coloured, and mineral and/or organic. Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

Among the organic pigments that may be mentioned are carbon black, pigments of D&C type and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment and also nacreous pigments based on bismuth oxychloride.

Among the water-soluble dyes, mention may be made of the disodium salt of ponceau, the disodium salt of alizarin green, quindine yellow, the trisodium salt of amaranth, the disodium salt of tartrazine, the monosodium salt of rhodamine, the disodium salt of fuchsin, xanthophyll and methylene blue.

Among the liposoluble dyes, mention may be made of Sudan Red III (CTFA: D&C Red 17), lutein, quinizarine green (CTFA: D&C Green 6), alizurol purple SS (CTFA: D&C Violet 2), Sudan Brown, D&C Yellow 11, D&C Orange 5, quinoline yellow, curcumin, and carotenoid derivatives such as lycopene, beta-carotene, bixin or capsanthin, and mixtures thereof. The colouring polymers are generally copolymers based on at least two different monomers, at least one of which is a monomeric organic dye. Such polymeric dyes are known to those skilled in the art. Reference may be made, for example, to the following documents: U.S. Pat. Nos. 5,032,670; 4,999,418; 5,106,942; 5,030,708; 5,102,980; 5,043,376; 5,104,913; 5,281,659; 5,194,463; 4,804,719; WO 92/07913 or EP 1 048 282.

The colouring ink may comprise one or more dyestuffs, especially photochromic pigments, i.e. dyestuffs which have the property of changing colour when they are irradiated with a light source of a certain frequency, and then of regaining their initial colour, or a similar colour, when the irradiation is stopped. Among the photochromic dyestuffs, mention may be made especially of:

complex mineral photochromic compounds and more particularly doped aluminosilicates and metal oxides and metal oxide hydrates, such as those described in WO-A-02/36083;

photochromic naphthopyran compounds, especially 3H-naphtho[2,1-b]pyrans or 2H-naphtho[1,2-b]pyrans, for instance 3,3-bis(4-methoxyphenyl)-6-morpholino-3H-naphtho[2,1-b]pyran, 3-phenyl-3-(4-morpholinophenyl)-6-morpholino-3H-naphtho[2,1-b]pyran, 3-phenyl-3-(4-piperidinophenyl)-6-morpholino-3H-naphtho[2,1-b]pyran, 3-phenyl-3-(4-piperidinophenyl)-6-carboxymethyl-9-N-dimethyl-3H-naphtho[2,1-b]pyran or 2-phenyl-2-(4-piperidinophenyl)-5-carboxymethyl-9-N-dimethyl-2H-naphtho[1,2-b]pyran. Such compounds are described in patent application EP-A-1 410 785;

diarylethene or fulgide compounds such as those described in patent application EP-A-938 887.

The colouring ink may also comprise one or more fillers, especially in a content ranging from 0.01% to 50% by weight, relative to the total weight of the colouring ink, preferably ranging from 0.01% to 30% by weight.

The term "fillers" should be understood as meaning colourless or white, mineral or synthetic particles of any shape, which are insoluble in the medium of the colouring ink, irrespective of the temperature at which this ink is manufactured.

These fillers serve especially to modify the rheology or texture of the colouring ink.

The fillers may be mineral or organic and of any shape, platelet-shaped, spherical or oblong, irrespective of the crystallographic form (for example lamellar, cubic, hexagonal, orthorhombic, etc.). Mention may be made of talc, mica, silica, kaolin, polyamide (Nylon®) powder (Orgasol® from Atochem), poly-β-alanine powder and polyethylene powder, tetrafluoroethylene polymer (Teflon®) powder, lauroyllysine, starch, boron nitride, hollow polymer microspheres such as polyvinylidene chloride/acrylonitrile microspheres, for instance Expancel® (Nobel Industrie), acrylic acid copolymer microspheres (Polytrap® from the company Dow Corning) and silicone resin microbeads (for example Tospearls® from Toshiba), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

The colouring ink may also comprise an additional polymer such as a film-forming polymer. Among the film-forming polymers that may be used in the colouring ink, mention may be made of synthetic polymers, of radical type or of polycondensate type, polymers of natural origin and mixtures thereof, in particular acrylic polymers, polyurethanes, polyesters, polyamides, polyureas, and cellulose-based polymers, for instance nitrocellulose.

Needless to say, a person skilled in the art will take care to select this or these optional additional compound(s), and/or the amount thereof, such that the advantageous properties of the colouring ink are not, or are not substantially, adversely affected by the envisaged addition.

Cosmetically Acceptable Medium

The colouring ink according to the invention constitutes a cosmetically acceptable medium, i.e. a medium that is compatible with keratin materials such as the skin of the face or the body, the lips, the hair, the eyelashes, the eyebrows and the nails.

Printing on the Transfer Surface

The term "digital printer" means a machine for printing in the form of pixels using digital data, different from a machine comprising a printing form. The printer may be an inkjet printer, for example a thermal or piezoelectric printer, a sublimation printer or a laser printer.

In one example, the printer is a laser printer arranged to allow the formation by electrophotography or magnetophotography of a coat of ink having a pattern on a transfer surface using at least one cosmetic toner and to deliver the toner present on the transfer surface in a state that is sufficiently free to allow it to be taken up or transferred by contact with the human keratin materials.

The term "cosmetic toner" should be understood as meaning a pulverulent cosmetic composition that is compatible with the formation of an image via an electrophotographic or magnetophotographic process as used in laser printers. Preferably, it is a toner that is suitable for electrophotographic use.

The toner is cosmetic in the sense that it is compatible with an application to human keratin materials. Depending on the surface to be made up, the formulation of the toner may be different. For example, for an application to the hair or the nails, it is possible to use certain compounds that might not be used for an application to the lips, for example.

The printer may be a food-grade inkjet printer such as the Gatocopy A426 machine allowing printing onto non-flat objects.

The printing may use several different inks, especially inks of different colours.

The printing may use at least three, especially at least four, five, six, seven, eight, nine, ten, eleven or twelve cosmetic inks of different colours.

The printing may use only colouring inks that produce primary colours. As a variant, the printing may use both colouring inks that produce primary colours and at least one ink that produces a non-primary colour.

In one variant, the printing may use colouring inks that produce black and/or white.

The printing of the ink may be three-colour or four-colour printing.

The pattern obtained by printing may comprise several areas of different colours. As a variant, the pattern obtained by printing is a flat tint.

The pattern formed by the cosmetic ink printed on the transfer surface may be of any type.

This pattern may reproduce the appearance of relief and/or colour heterogeneities of the skin, for example freckles or a mole.

The pattern formed by the colouring ink borne by the transfer surface may be coloured when observed under white light in the visible region (400 nm-800 nm). As a variant, the pattern is colourless under white light in the visible region, but may appear coloured when submitted to a chemical and/or energy stimulus, such as exposure to UV (365 nm-400 nm), for example when the colouring ink contains a photochromic or fluorescent dyestuff.

The colouring ink obtained by printing may be deposited in the form of spots and/or of raster lines, so as to form a halftone image, for example a monochromatic or polychromatic image.

The pattern formed by the colouring ink printed on the transfer surface may be of any type.

This pattern may reproduce the appearance of relief and/or colour heterogeneities of the skin, for example freckles or a mole.

The printing may also follow geometrical rectification rules. In so far as the transfer surface is deformable, during the application, the pattern may be geometrically deformed (for example extension in one of the two dimensions). As a result, the pattern is printed with a geometrical deformation (in the present case reduction according to the deformable dimension(s)) such that, after application, the pattern is at the desired scale. Geometrical rules: either universal or specific, may be applied to the pattern to be printed on the transfer surface so that the pattern has the desired form after transfer onto the area of the keratin materials to be treated. The use of such rectification rules is particularly advantageous with a substrate that has a transfer surface bearing reliefs, in particular in order to embrace the form of an imprint, as will be seen later. Use may be made in particular of specific geometrical rules adapted to the area to be treated and/or to the desired pattern.

The colouring ink may be liquid at the time of printing and may have, for example, a viscosity ranging from 1 mPa·s to 500 mPa·s and preferably from 1 mPa·s to 300 mPa·s at 25° C.

The viscosity of an ink of the invention may be measured via any process known to those skilled in the art, and especially according to the following conventional process. At 25° C. using a Rheomat 180 viscometer, equipped with a spindle rotating at 200 rpm, a person skilled in the art can select the spindle for measuring the viscosity from the spindles M1, M2, M3 and M4 on the basis of their general knowledge, so as to be able to perform the measurement.

The colouring ink may be in emulsion form.

Advantageously, the colouring ink is not entirely dry on the substrate when it is applied to the keratin materials. The colouring ink may be in fluid form when it is applied to the keratin materials.

When the ink is in the form of a cosmetic toner, this toner may comprise, besides a colouring agent, a compound for controlling the electrical charge, a particular additional filler, a lubricant, a wax and/or a binder.

Preferably, the particles of the toner have a mean size of between 1 and 16 μm. The toner consists, for example, of pigments with a particle size in particular of between 1 and 10 μm.

All or part of the colouring ink borne by the transfer surface may be applied by transfer to the keratin materials.

In one embodiment example, at least 25% by mass, especially 50%, especially 75% and especially substantially all of the coat of colouring ink initially present on the transfer surface is applied by transfer to the keratin materials.

In one embodiment example, the application of the colouring ink is performed by application with pressure of the transfer surface onto the keratin materials.

Substrate and Transfer Surface

In one embodiment example, the substrate used in the invention comprises at least one translucent or transparent area.

The translucent or transparent area allows a user to see through the substrate and thus to visualize more easily the surface to be made up and/or treated before transferring the cosmetic ink. The presence of a translucent or transparent area thus advantageously contributes towards facilitating the production of a precise makeup result on the keratin materials.

The translucent or transparent area of the substrate can be totally or partly superposed with the layer of cosmetic ink, and especially may overlap with it.

The layer of cosmetic ink may be superposed in its entirety on the translucent or transparent area of the substrate. As a variant, only part of the layer of cosmetic ink is superposed on the transparent area of the substrate.

The substrate may be made of a transparent or translucent material. In this case, the translucent or transparent area extends over the entire surface of the substrate.

As a variant, the substrate is opaque over all or part of its surface.

The substrate may comprise a material in sheet form, especially a transparent material.

The substrate may be a flexible sheet or a rigid plate. It may be made of plastic (for example polyethylene or polystyrene). It may be woven or nonwoven. It may be made of organic or mineral material. It may be an aluminium foil.

The substrate is preferentially based on a non-absorbent material, for example a plastic film. The substrate is advantageously non-porous, at least on the face intended to receive the print.

The transfer surface may retain the cosmetic ink by capillary action.

The transfer surface can be planar or non-planar.

The transfer surface of the substrate may be defined by all or part of: the outer surface of an applicator roller, the surface of an applicator pad, an element in sheet form, a patch, the surface of a porous foam, especially a sponge or a wipe, a coarse brush, a fine brush or a flocked tip.

The applicator roller may have the form of a right cylinder. In one variant, the roller has the form of an irregular cylinder, for example the form of an hour glass.

In one variant, the roller is "premoulded", i.e. it has an initial non-flat form corresponding to the general form of the area to be made up, for example the negative of the lips, of an eye socket, of an ankle or of a forearm.

In one variant, the substrate is plated at the time of transfer against an imprint of the area to be made up, so that the transfer surface reproduces the relief of the area to be made up.

The transfer surface is defined, for example, by all or part of the surface of a deformable sheet mounted on the surface of an applicator roller or a pad.

The transfer surface may be elastically deformable. Thus, in a first configuration, the transfer surface may be flat, and, in a second configuration, the transfer surface may be incurved.

In one variant, the substrate is configured so that the transfer surface takes a first form, for example substantially flat, during printing, and a second form, different from the first, during the application of the colouring ink to the keratin materials. The second form advantageously corresponds to the form of the surface of the keratin materials intended to be coated with the colouring ink, for example the form of the nails or of a part of the face.

The substrate is preferentially based on a non-absorbent material, for example a plastic film. The substrate is advantageously non-porous, at least on the face intended to receive the print.

In one embodiment, when the colouring ink is intended to be applied to the cheeks and/or the nails, the substrate may have a thickness of greater than or equal to 1 mm, especially 3 mm, for example ranging from 1 to 5 mm.

In one embodiment example, when the colouring ink is intended to be applied to the area around the eyes and/or to the lips, the substrate may have a thickness of greater than or equal to 3 mm, especially 1 mm, for example ranging from 3 to 20 mm.

In one embodiment example, when the colouring ink is intended to be applied to the nose and/or in the area of the ears, the substrate may have a thickness of greater than or equal to 1 cm, especially 3 cm, for example ranging from 1 to 4 cm.

Thus, the substrate advantageously has a thickness adapted to the area of keratin materials to be made up.

The thickness of the substrate corresponds to its maximum dimension measured perpendicular to the transfer surface.

The substrate may have a variable thickness.

The substrate may be premoulded.

In one embodiment example, the substrate comprises an indication printed or not with the same ink as that intended to be transferred. The indication states, for example, the nature of the keratin materials intended to be made up with the colouring ink or illustrates to scale, enlarged, reduced or otherwise and "right-side up" the pattern deposited "wrong-side up" on the substrate.

In one embodiment example, the transfer surface is detachable from a part of the substrate.

The substrate may be reusable.

For example, printing is performed on the substrate, which is accessible for the transfer, but does not leave the printer. Thus, after use, the printer can reintegrate the substrate, clean it and make it ready for a new print.

According to another aspect, a subject of the invention is an assembly for performing the makeup process according to the invention as described previously, comprising:
- at least one device comprising a substrate having a transfer surface and a coat of at least one cosmetic colouring ink borne by the transfer surface, obtained by printing using at least one digital printer,
- at least one composition, comprising a film-forming polymer, which is capable of forming a protective coating on an area of the keratin materials to be made up, the composition being contained in a packaging assembly.

The assembly may comprise the same case for containing the device and the composition.

The assembly may also comprise a manual application system for forming the protective coating.

Measurement of the Ability of the Colouring Ink to Transfer without the Need to Add an Intermediary Fluid Compound As mentioned above, the colouring ink is, particularly preferably, capable of transferring onto the keratin materials without the addition of an intermediary fluid compound.

To check whether a given colouring ink has this property, the coat of colouring ink under consideration borne by a surface is placed in contact with a sample of artificial skin sold by the company Beaulax under the brand name Bioskin ref #white 061031-2.

The contact is performed for a time of 1 s by applying a pressure of 5000 pascals (i.e. 50 g/cm$^2$) under atmospheric temperature and pressure conditions (20° C. and 1 bar). No intermediary fluid compound is added either to the colouring ink or to the sample before or during the contact.

A visual evaluation is performed.

If the colouring ink transfers onto the keratin materials, then the colouring ink is considered as being capable of transferring onto the keratin materials without the addition of an intermediary fluid compound.

DESCRIPTION OF THE FIGURES

The invention may be understood more clearly on reading the following description of non-limiting implementation examples thereof, and on examining the attached drawing, in which:

FIG. 1 shows an example of a makeup device used in a makeup process according to the invention, FIG. 2 is a section along II-II of the makeup device of FIG. 1, FIGS. 3 to 6 represent different steps of an example of a makeup process according to the invention, FIG. 7 shows an example of a cosmetic assembly according to the invention, FIG. 8 shows an example of a transfer makeup application obtained via a process according to the invention, and FIGS. 9a and 9b illustrate examples of transfer makeup applications, with and without the coating according to the invention.

FIGS. 1 and 2 show a makeup device 1 according to the invention, comprising a substrate 2 whose front side defines a transfer surface 3. The device 1 may, as illustrated, have only one face defining the transfer surface 3, bearing a coat 4 of at least one cosmetic colouring ink according to the invention.

In one variant, not shown, two transfer surfaces 3 are defined by the two opposite faces of the substrate 2. In this case, these surfaces may bear coats of different cosmetic colouring inks, these coats possibly differing by their colour, the nature of the colouring inks borne and/or by the patterns formed.

In the device 1 illustrated in FIGS. 1 and 2, the coat of colouring ink 4 borne by the transfer surface 3 was deposited by printing using a digital printer, which deposits the ink spots in correspondence with the pixels of an image to be reproduced, for example in the form of raster frames. This coat 4 is not entirely dry at the time of application to the keratin materials.

The coat 4 may form any type of pattern, for example in the form of a heart as illustrated.

The substrate 2 may have at least one non-opaque area 5, which is transparent or translucent, and which may totally or partly be superposed with the coat 4. The transparent area 5 allows the user to see through the substrate 2 and thus to visualize the surface to be made up through the device 1 when this device is superposed on the said surface.

All of the coat 4 may, as illustrated, be superposed on the transparent area 5. In one variant, not shown, only part of the coat 4 is superposed on the transparent area 5.

The substrate 2 may be made of a transparent material. The transparent area 5 then extends over the entire surface of the substrate 2.

The substrate 2 may bear an indication 7, for example print, which gives information regarding a recommended positioning for the makeup, for example "right cheek" as illustrated, or a reproduction of the place and scale, reduced or not, of the pattern to be transferred or the nature of the keratin materials intended to be made up with the colouring ink, or the like, and may also provide information regarding the colour reference and/or the pattern.

The substrate 2 is preferably made of a flexible material. As a variant, the substrate 2 is made of a rigid or semi-rigid material.

All or part of the area of the transfer surface 3 superposed on the coat 4 is preferably smooth and has a roughness of less than or equal to 1 mm, especially between 1 and 100 µm and preferably less than or equal to 50 µm. The roughness is measured using a roughness meter, the tip of which has a radius of curvature of 10 mm, and the force of which, applied to the material to be characterized, is 6 mN.

FIGS. 3 to 6 schematically show various steps of an example of a makeup process according to the invention. As illustrated, the device 1 is first brought close to the area of skin P to be made up, which is preferably dry, so as to place the coat 4 in contact with the area of skin P to be made up, and the user then applies a pressure allowing the colouring ink to be transferred onto the area of skin P to be made up. During the contact with the keratin materials, the substrate 2 is preferably not moved sideways so as not to affect the appearance of the transferred pattern.

The pattern transferred onto the keratin materials corresponds to the pattern formed by the coat 4 when it is present on the substrate 2 (i.e. when it has not yet been transferred onto the keratin materials to be made up).

Next, as illustrated in FIG. 6, a coating 8 is formed, for example by spraying a composition C according to the invention as described above onto the coat of ink 4.

The coat of ink 4 is, for example, dry at the time of spraying. In one variant, the coating is formed on a coat of ink that is not entirely dry.

The composition C is sprayed, for example, using a pressurized packaging assembly 50 of aerosol type, actuated by the user.

FIG. 7 shows an embodiment example of a cosmetic assembly 30 according to the invention. This assembly comprises, in the same case, a plurality of devices 1 as described previously, each differing by the nature or form of the substrate 2 and/or by the pattern formed by the coat 4, especially its shape and/or its colour. The assembly also comprises a packaging assembly 50 containing a film-forming composition C intended to form a protective coating 8 on the coat of ink, once transferred onto the keratin materials. In the example illustrated, the composition C is contained in a container of aerosol type. In another variant, the composition is not sprayed, but is applied, for example, with a pad of cotton wool or a fine brush.

The case may be leaktight so as to prevent the inks from drying out. The case may be made with means for avoiding contact of the inks with a surface other than the transfer surface, so as to reduce the risk of premature transfer. For example, the case comprises a thermoformed shell whose wall extends a distance from the areas of the substrate that are covered with inks.

EXAMPLES

Example 1

In the Case of the Skin

This example corresponds to FIG. 8.

Four inks corresponding to the formulations given in the table below were prepared:

TABLE 1

|  | Yellow I | Magenta I | Cyan I | Black I |
|---|---|---|---|---|
| Dye | D&C Yellow 8 1% | FD&C Red 4 1% | FD&C Blue 1 1% | (1) 1% |
| Ethylene glycol |  | 4% | 6% | 5% |
| Diethylene glycol | 8% |  |  |  |
| 1,5-Pentanediol |  | 4% | 4% |  |
| 2-Pyrrolidone | 5% | 5% | 4% |  |
| Glycerol | 8% | 3% | 4% | 7% |
| 2-Imidazolidinone | 4% | 4% | 4% | 9% |
| Water | 76% | 79% | 77% | 78% |
| Total | 100% | 100% | 100% | 100% |

(1) Brown-Replacement-J from Sensient

These compositions are introduced into Canon printer cartridges and then used with a Canon Pixma IP100 inkjet printer.

Two identical patterns of cosmetic ink are printed on a plastic sheet.

This plastic sheet is placed on the surface of the skin. Simple pressure on the sheet suffices to transfer the ink, thus resulting, by transfer, in the appearance of two patterns. The sheet is removed.

A composition is then prepared according to Formula 1 below:

| Formula 1 | |
|---|---|
| Sulfopolyester sold under the name Eastman AQ 38 by the company Eastman Chemical | 15% (solids) |
| Water | qs 100% |

A pad of cotton wool is soaked with the composition and placed on one of the two patterns.

Next, the two patterns are stressed by washing with soap.

It is seen that the pattern covered with Formula 1 withstands this stress much better.

Example 2

The process is performed as in Example 1, and two identical patterns are produced on the skin.

The following formula is then prepared, and placed in a lacquer-type aerosol container.

Formula 2 is sprayed onto the surface above one of the two patterns, at a rate of 2 g per 100 cm$^2$.

| Formula 2 | |
|---|---|
| Acrylic acid/ethyl acrylate/N-tert-butylacrylamide terpolymer sold under the name Ultrahold Strong by the company BASF | 5 g |

| Formula 2 -continued | |
|---|---|
| Ethanol | 60 g |
| DME | 35 g |

Next, the two patterns are stressed with a succession of three 20-minute baths, with drying between each bath.

It is seen that the pattern covered with Formula 2 withstands this stress much better: whereas the pattern without the coating has virtually disappeared, the pattern formed by the coat of ink 4 covered with the protective coating 8 has kept its precision.

Example 3

An HP LaserJet Pro 400 M451 NW printer, modified to delete the heating member, is used.

The electronic system is modified to prevent an operating error following the removal of the heating roller. The thermistor used for measuring the temperature is especially replaced with a resistance simulating a temperature normally encountered of the heating roller.

Removal of the heating roller makes it possible to minimize the mechanical stresses during printing without melting the toners.

The following preparation is used as cosmetic toners: A toner of an HP Laser jet pro Color M451nw printer is taken. After opening, the existing powder is removed and replaced with a powder (40 g) containing 6 g of ferrite, 33 g of carbon black powder and 1 g of calcium carbonate, rendered pulverulent by blending with aeration.

Printing is performed on a sheet of transparent type for a Laser printer.

The printed pattern is applied by transfer onto the skin just after printing. The sheet is placed on the skin with a pressure of 50 g/cm$^2$ for 5 seconds. The sheet is then removed.

To complete the makeup, a composition intended to form a protective coating, containing a resin, is sprayed on, at a distance of 30 cm. To do this, an Elnett® brand hair lacquer is used. It is left at rest for 1 minute. The makeup application is then complete.

The expression "comprising a" should be understood as being synonymous with "comprising at least one".

The expression "between . . . and . . . " or "ranging from . . . to . . . " should be understood as including the limits.

The invention claimed is:

1. A method for making up an area of human keratin materials using a makeup device having a transfer surface and a not entirely dry coat of at least one digitally printed cosmetic colouring ink borne by the transfer surface in which the at least one digitally printed cosmetic colouring ink is configured to be applied to the keratin materials, the method comprising:

transferring at least part of the not entirely dry coat of cosmetic ink onto the area to be made up, which is dry, by placing the not entirely dry coat of ink in contact with the area to be made up, the ink comprising one or more water-soluble dyes, without addition of an intermediary fluid compound, and then forming a protective coating by applying at least one composition comprising a film-forming polymer, onto the area of keratin materials to be made up.

2. The method according to claim 1, the protective coating being transparent.

3. The method according to claim 1, comprising moving the transfer surface away from the area of the human keratin materials after the coat of ink has been transferred.

4. The method according to claim 1, the composition comprising a solvent chosen from water and volatile organic solvents.

5. The method according to claim 1, the composition being applied using a manual application system or by propulsion.

6. The method according to claim 1, the ink(s) being deposited onto the transfer surface without being covered and without covering a layer of an adhesive.

7. An assembly for performing the makeup method according to claim 1 comprising:
   the makeup device comprising a substrate having the transfer surface and the coat of at least one digitally printed cosmetic colouring ink borne by the transfer surface the coat of cosmetic coloring ink being not entirely dry, the ink comprising the one or more water soluble dyes, without addition of an intermediary fluid component; and being transferable onto the area to be made up, which is dry,
   the at least one composition, comprising the film-forming polymer, which is capable of forming a protective coating on an area of the keratin materials to be made up, the composition being contained in a packaging assembly.

8. The assembly according to claim 7, the substrate and the composition being contained in the same case.

9. The assembly according to claim 7, comprising a manual application system for forming the protective coating.

10. The method according to claim 1, the film-forming polymer being a vinyl film-forming polymer resulting from the polymerization of ethylenically unsaturated monomers containing at least one acid group and/or esters of these acid monomers and/or amides of these acid monomers.

11. The method according to claim 1, the film-forming polymer being a polyester obtained by polycondensation of dicarboxylic acids with polyols.

12. The method according to claim 1, the film-forming polymer being an isophthalate/sulfoisophthalate copolymer.

13. The method according to claim 1, the film-forming polymer is present in the composition in a solids content ranging from 0.01% to 20% by weight relative to the total weight of the composition.

14. A method for making up an area of human keratin materials using a makeup device comprising:
   providing a makeup device having a transfer surface and a coat of at least one digitally printed cosmetic colouring ink borne by the transfer surface in which the at least one digitally printed cosmetic colouring ink comprises one or more dyestuffs chosen from water-soluble dyes and is configured to be applied to the keratin materials,
   transferring at least part of the not entirely dry coat of cosmetic ink onto the area to be made up, which is dry, by placing the coat of ink in contact with the area to be made up, without addition of an intermediary fluid compound, and then
   forming a protective coating by applying at least one composition comprising a film-forming polymer, onto the area of keratin materials to be made up.

* * * * *